US008228666B2

(12) United States Patent
Rickard (10) Patent No.: US 8,228,666 B2
(45) Date of Patent: Jul. 24, 2012

(54) RETROFIT CONTROL SYSTEM AND POWER SUPPLY FOR A TATTOO GUN

(76) Inventor: Timothy Garett Rickard, Portland, OR (US)

( * ) Notice: Subject to any disclaimer, the term of this patent is extended or adjusted under 35 U.S.C. 154(b) by 607 days.

(21) Appl. No.: 12/381,919

(22) Filed: Mar. 17, 2009

(65) Prior Publication Data
US 2010/0241151 A1  Sep. 23, 2010

(51) Int. Cl.
*H05K 5/00* (2006.01)
*H05K 7/00* (2006.01)
*A61B 17/34* (2006.01)
*H01R 11/22* (2006.01)

(52) U.S. Cl. ........... 361/679.01; 361/679.03; 361/679.4; 606/185; 606/186; 439/829

(58) Field of Classification Search .................. 361/622, 361/679.01, 679.03, 679.4; 606/185–186; 439/829
See application file for complete search history.

(56) References Cited

U.S. PATENT DOCUMENTS

| | | | |
|---|---|---|---|
| 4,159,659 A * | 7/1979 | Nightingale | 81/9.22 |
| 6,017,354 A * | 1/2000 | Culp et al. | 606/170 |
| 6,108,197 A * | 8/2000 | Janik | 361/679.03 |
| 6,550,356 B1 * | 4/2003 | Underwood | 81/9.22 |
| 6,596,007 B2 * | 7/2003 | Evans | 606/186 |
| 6,697,894 B1 * | 2/2004 | Mitchell et al. | 710/73 |
| 6,772,656 B2 * | 8/2004 | Godoy et al. | 81/9.22 |
| 6,774,754 B2 * | 8/2004 | Evans | 335/256 |
| 7,207,242 B1 * | 4/2007 | Daigle | 81/9.22 |
| 7,442,042 B1 * | 10/2008 | Lewis | 439/39 |
| 2002/0087179 A1 * | 7/2002 | Culp et al. | 606/167 |
| 2003/0002243 A1 * | 1/2003 | Newman et al. | 361/683 |
| 2003/0090162 A1 * | 5/2003 | Cornog et al. | 307/150 |
| 2003/0199863 A1 * | 10/2003 | Swanson et al. | 606/40 |
| 2004/0097117 A1 * | 5/2004 | Gonnering | 439/218 |
| 2005/0082915 A1 * | 4/2005 | Steinberg | 307/147 |
| 2005/0272401 A1 * | 12/2005 | Zatezalo et al. | 455/347 |
| 2006/0064080 A1 * | 3/2006 | Cao | 606/10 |
| 2006/0217700 A1 * | 9/2006 | Garito et al. | 606/34 |
| 2007/0250098 A1 * | 10/2007 | Malackowski et al. | 606/170 |
| 2008/0089067 A1 * | 4/2008 | Grosjean | 362/285 |
| 2008/0300615 A1 * | 12/2008 | Colton et al. | 606/186 |
| 2009/0125049 A1 * | 5/2009 | Copeland et al. | 606/186 |
| 2009/0280667 A1 * | 11/2009 | Pallino et al. | 439/269.1 |
| 2010/0051595 A1 * | 3/2010 | Diedrick et al. | 219/137 R |
| 2010/0072827 A1 * | 3/2010 | Norstrom | 307/112 |

* cited by examiner

*Primary Examiner* — Bradley Thomas
(74) *Attorney, Agent, or Firm* — Mark S. Hubert (57) ABSTRACT

A battery powered portable system of operating a tattoo gun that can be worn on the user's arm or clipped to the user's belt. The system directly connects to conventional tattoo guns, and offers the options of utilizing a fingertip control of the machine's speed and ON/OFF functions or the conventional control module and foot pedal controls.

10 Claims, 7 Drawing Sheets

RETROFIT CONTROL SYSTEM AND POWER SUPPLY FOR A TATTOO GUN

BACKGROUND OF THE INVENTION

The present invention relates to a device that can replace the power supply, control module and foot pedal operational switch that is used to operate a conventional tattoo gun. More particularly, to a battery powered portable system of operating a tattoo gun that can be worn on the user's arm, offers fingertip control of the machine's speed and ON/OFF functions, and can be directly substituted in place of the detachable power cord found in the industry standardized tattoo machines.

A conventional, prior art tattoo machine has four major components; a tattoo gun, an operational foot switch, a connector cable, and a control unit. The control unit is a bulky enclosure that is connected to an AC power source and has an AC/DC transformer that outputs DC power to a small DC oscillating motor located on the tattoo gun that rapidly strokes the inking needle. The voltage of the DC power output is manually adjusted on the control unit to change the speed of the motor. The operational foot switch allows DC power to the tattoo gun through the connector cable. In operation, the tattoo artist has to go back and forth between the control unit to adjust the needle speed and has to start and stop the needle with the foot pedal. This is awkward to operate and the artist is somewhat constrained by the length of the connector cable.

There are newer DC operated portable tattoo machines available but these have problems. They are sold as complete units that are very expensive. Additionally, most tattoo artists work and develop their artistic skills with the same tattoo guns for years and are accustomed to the weight, balance, feel and response of that gun. They are not inclined to change. The retrofit control system and power supply is an electronic DC power supply unit with interchangeable batteries that has an LCD visual interface, a spring loaded tattoo gun connection clip with a speed adjustment means thereon, and a fingertip microswitch that can be removably mounted on the tattoo gun where the artist prefers. It is small and light enough to be worn on the arm of the tattoo artist in an elastic pouch.

The retrofit control system and power supply fulfills a long felt need in the field of tattoo machines. It allows tattoo artists freedom of movement, portability, fingertip control of the gun's operation and speed, and a visual status of battery condition and operating parameters. This new invention utilizes and combines known and new technologies in a unique and novel configuration to overcome the aforementioned problems of the prior art.

SUMMARY OF THE INVENTION

The general purpose of the present invention, which will be described subsequently in greater detail, is to provide a retrofit control and DC power supply system that is able to connect to existing tattoo guns without any modifications. It has many of the advantages mentioned heretofore and many novel features that result in a new invention which is not anticipated, rendered obvious, suggested, or even implied by any of the prior art, either alone or in any combination thereof.

In accordance with the invention, an object of the present invention is to provide an improved retrofit control and DC power supply system for a tattoo gun that is small and light enough to be worn on the arm or clipped to a belt.

It is another object of this invention to provide an improved retrofit control and DC power supply system for a tattoo gun capable of uninterrupted operation through the use of multiple rechargeable, replaceable batteries.

It is a further object of this invention to provide a retrofit control and DC power supply system for a tattoo gun that gives the artist a visual status of the battery condition and the tattoo gun speed setting.

It is still a further object of this invention to provide for a retrofit control and DC power supply system for a tattoo gun that incorporates an ON/OFF switch that may be removably mounted on the barrel of the gun.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements. Other objects, features and aspects of the present invention are discussed in greater detail below.

BRIEF DESCRIPTION OF THE DRAWINGS

FIG. 6 illustrates the alternate embodiment retrofit control system and power supply for a tattoo gun with the side cover plate on;

DETAILED DESCRIPTION

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

Figure 1:
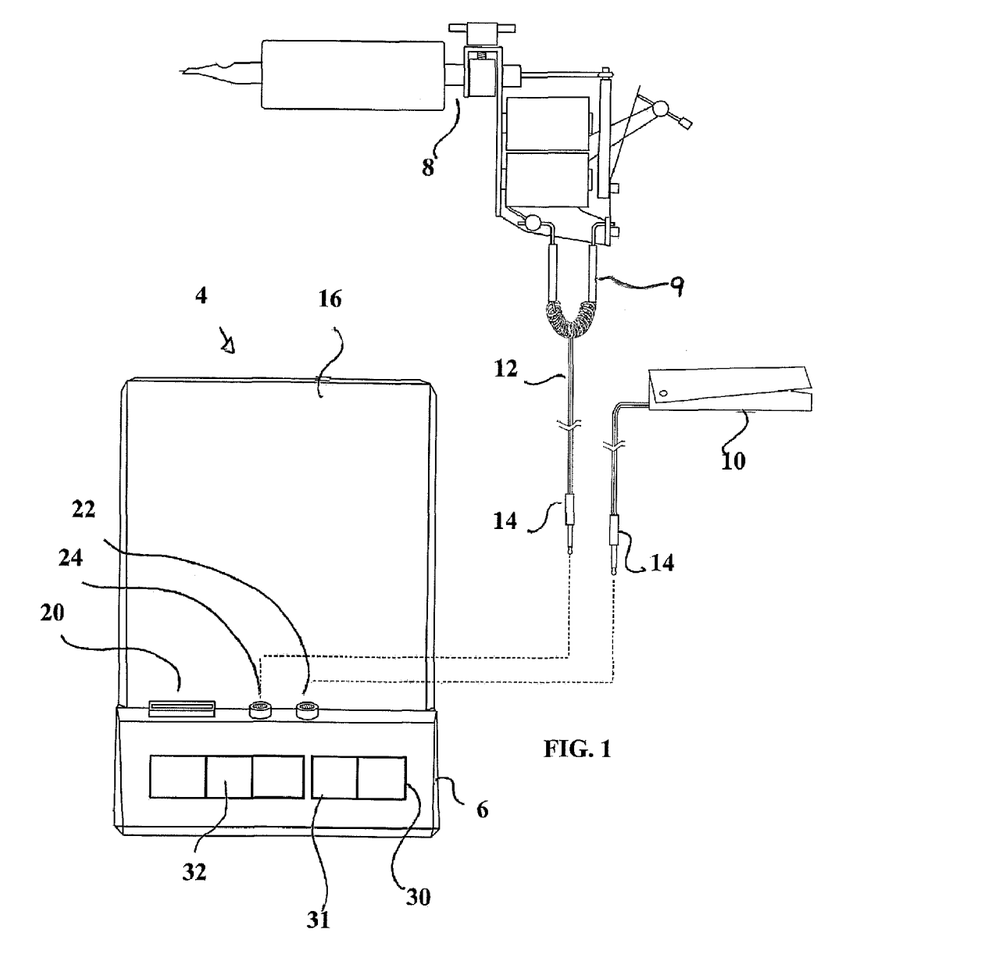
FIG. 1 is a top view of the retrofit control and DC power supply system connected to a tattoo gun in the conventional configuration showing the general arrangement of all components.
Figure 2:
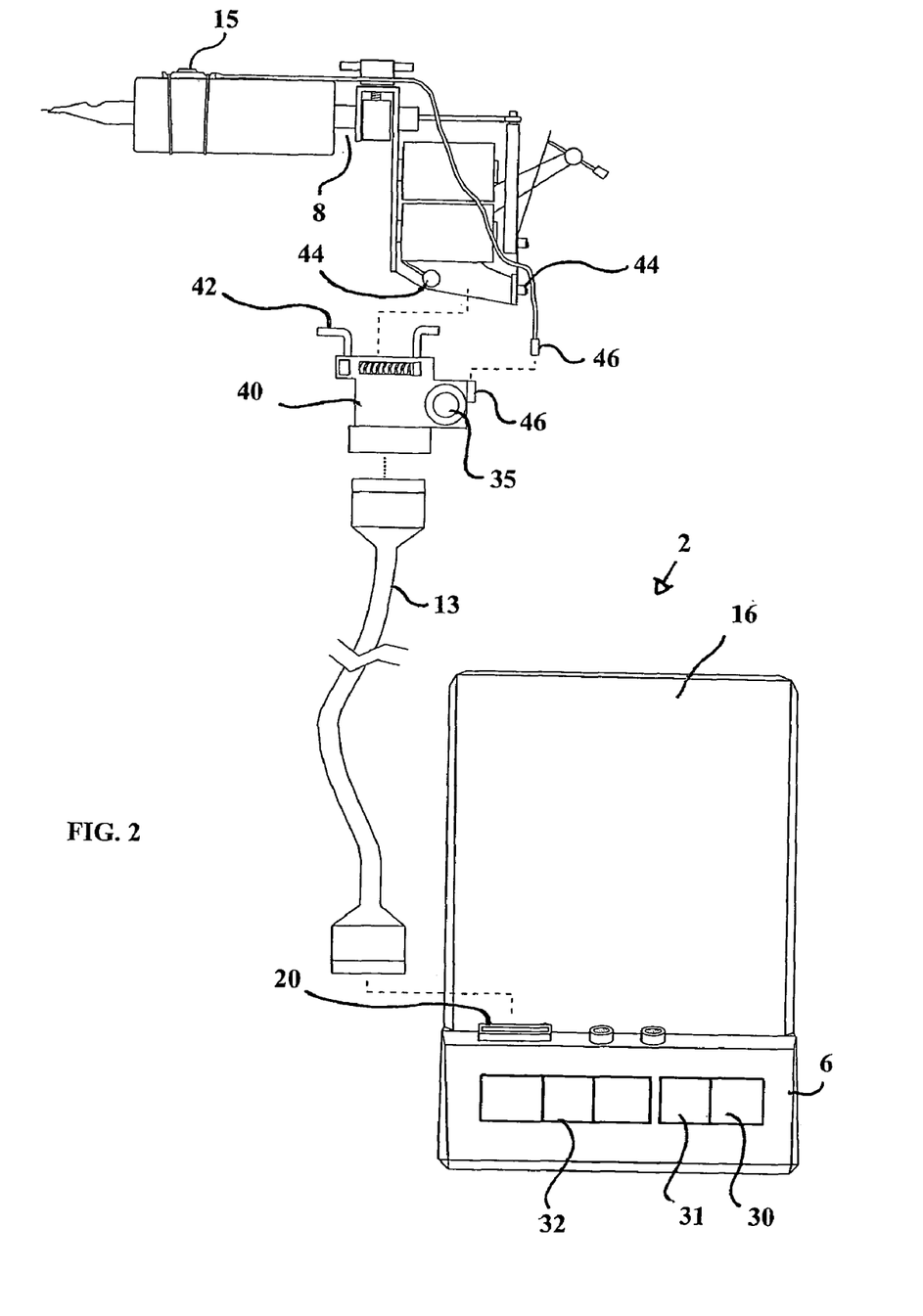
FIG. 2 is a top view of the retrofit control and DC power supply connected to a tattoo gun in the preferred configuration showing the general arrangement of all components.

The retrofit control and DC power supply system (system) is configured in a conventional embodiment 4 (FIG. 1) and a preferred embodiment 2 (FIG. 2). Each of these embodiments utilize the same control unit 6 and the same tattoo gun 8 but differ in the components connected to these. The conventional system 4 has a jack connectable foot switch 10 and a jack connectable first spring clip power cable 12. Although each of these are shown connecting to the control unit 6 with input jack connectors 14 it is well known in the art that there is a plethora of electrical connectors or hard wiring that would accomplish the same task. The preferred embodiment system 2 has only a pin connector attached second spring clip power cable 13 connected to a spring clip power connector 40 with a removably connected tactile remote switch 15 attached thereto.

The control unit 6 utilized in each of the embodiments has an outer casing that houses the printed circuit board with the operational circuit components thereon, a battery 16, the first spring clip power control cable pin connector 20, the second spring clip power cable jack connector 24, the foot switch cable jack connector 22, the display interface 26, the power button 30, the battery status indicator button 31 and the speed (tattoo gun voltage) control buttons 32. The outer casing has a belt clip 28 affixed to its bottom face. The operational circuit 34 (FIG. 5) that is used in both embodiments is identical although different electrical pathways are utilized for the operation of the foot switch 10 and the speed control buttons 32 versus the tactile switch 15 and the speed adjustment potentiometer 35.

Figure 3:
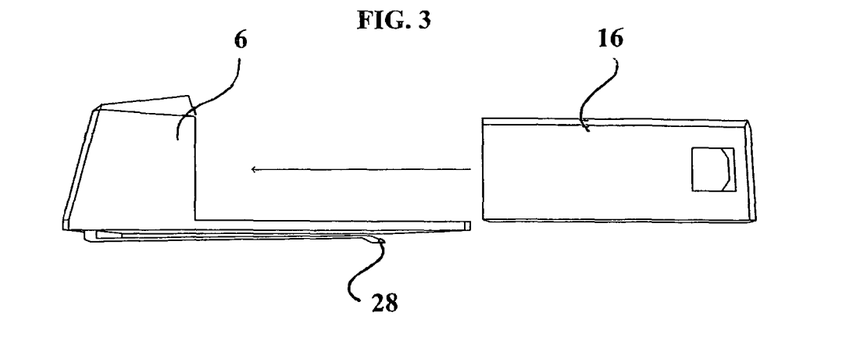
FIG. 3 is a side view of the retrofit control and DC power supply system control unit and removable battery.
Figure 4:
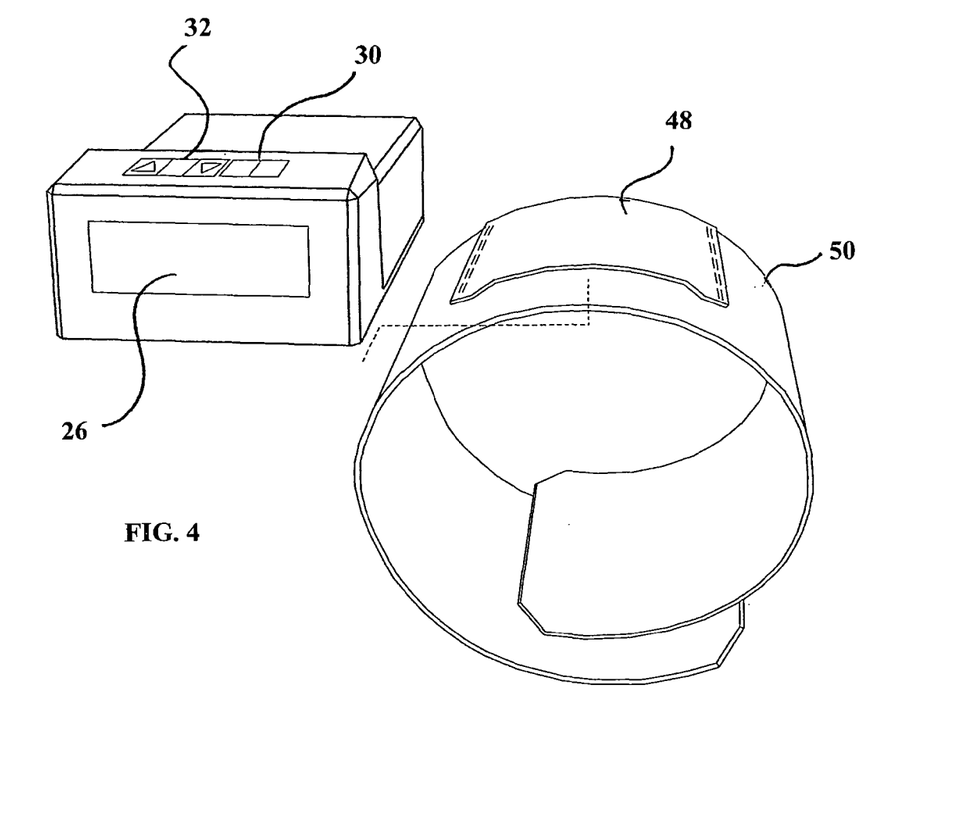
FIG. 4 is a perspective view of the retrofit control and DC power supply system control unit with installed battery and the elastic arm strap.

Looking at FIG. 3 it can be seen that the replaceable, rechargeable battery 16 slideably engages into control unit 6 so as to matingly connect their electrical contacts as is well known in the industry and not illustrated. When the electrical contacts are engaged fully the battery 16 and control unit 6 are a mechanically interlocked solid unit. This is accomplished through the use of physically engageable configurations which require the depression of unlock buttons 18 on the battery 16 as is well known in the field of battery powered devices and not discussed or illustrated in detail herein.

In the preferred embodiment 2 the first spring clip power control cable 13 plugs into spring clip power connector 40 that houses thereon a tactile switch 15 (that is used rather than the foot control switch 10) and a speed adjustment potentiometer 35 (that is used rather than speed control buttons 32.) The first spring clip power control cable 13 has conventional pin connectors on both its distal and proximate ends that connect to the control unit 6 and the spring clip power connector 40. The spring clip power connector 40 has a pair of spring loaded arms 42 that open and close to engage a pair of matingly conformed contactors 44 that are located on the gun 8 and provide the power to the gun. It also has a speed adjustment potentiometer 35 integrated therein and a detachable tactile switch 15 connected by plug connector halves 46. The tactile switch 15 switches on and off the power to the gun 8 and is mountable anywhere on the gun 8 by mechanical means such as rubber bands, cable ties, glue or screws, however the likely location for mounting would be the top surface of the tattoo gun's barrel where the artist's index finger could readily access it. When in the preferred configuration, the speed control buttons 32 do not function as this function is now operated through the speed adjustment potentiometer 35. The preferred embodiment 2 does not have the foot switch 10 or the second spring clip power cable 12 plugged into the control unit 6.

The preferred embodiment unit 2 is retrofit onto a conventional tattoo machine by simply disengaging the conventional spring cable and engaging the distal end of the first spring clip power control cable 14 into the spring clip power connector 40, then manipulating the pair of spring loaded arms 42 to engage the contactors 44 on the tattoo gun 8 the connecting the proximate end of the first spring clip power control cable 14 to a control unit 6 with an operable battery 16 installed. Finally, the tactile switch 15 is coupled to the spring clip power connector 40 via the plug connector halves 46 and mechanically affixed to the tattoo gun 8.

In operation, the preferred embodiment 2 once connected is switched on via the power indicator button 30, and the battery status button 31 is depressed to display the battery voltage, then depressed again to display the tattoo gun voltage in the display interface 26. The preferred embodiment 2 is slid into the elastic pocket 48 on the elastic arm band 50 such that the display interface 26 is visible, and then the entire unit is slid onto the artist's arm. (Optionally the entire unit may be clipped onto the artist's belt.) The artist adjusts the speed adjustment potentiometer 35 to adjust the voltage to make the tattoo gun 8 operate at the desired speed and then depresses the tactile switch 15 as needed to ink the patron. In this preferred embodiment the speed control buttons 32 are electronically bypassed and the potentiometer 35 handles this function.

The conventional embodiment unit 4 is retrofit onto a conventional tattoo machine by simply engaging the jack 14 on the first spring clip power cable 12 into the spring clip power cable jack connector 24, and engaging the jack 14 on the foot switch 10 into the foot switch cable jack connector 22 on control unit 6 since the spring clip 9 is already connected to the conventional tattoo machine it came from.

In operation, the conventional embodiment 4 once connected is switched on via the power indicator button 30, and the battery status button 31 is depressed to display the battery voltage, then depressed again to display the tattoo gun voltage in the display interface 26. The preferred embodiment 2 is slid into the elastic pocket 48 on the elastic arm band 50 such that the display interface 26 is visible, and then the entire unit is slid onto the artist's arm. (Optionally the entire unit may be clipped onto the artist's belt.) The artist adjusts the speed adjustment buttons 32 to make the tattoo gun 8 operate at the desired speed as indicated on the display interface 26 and then depresses the foot switch 10 as needed to ink the patron. In this conventional embodiment 4 the speed control buttons 32 and the foot switch 10 operate to allow the inking of the patron.

Figure 5:
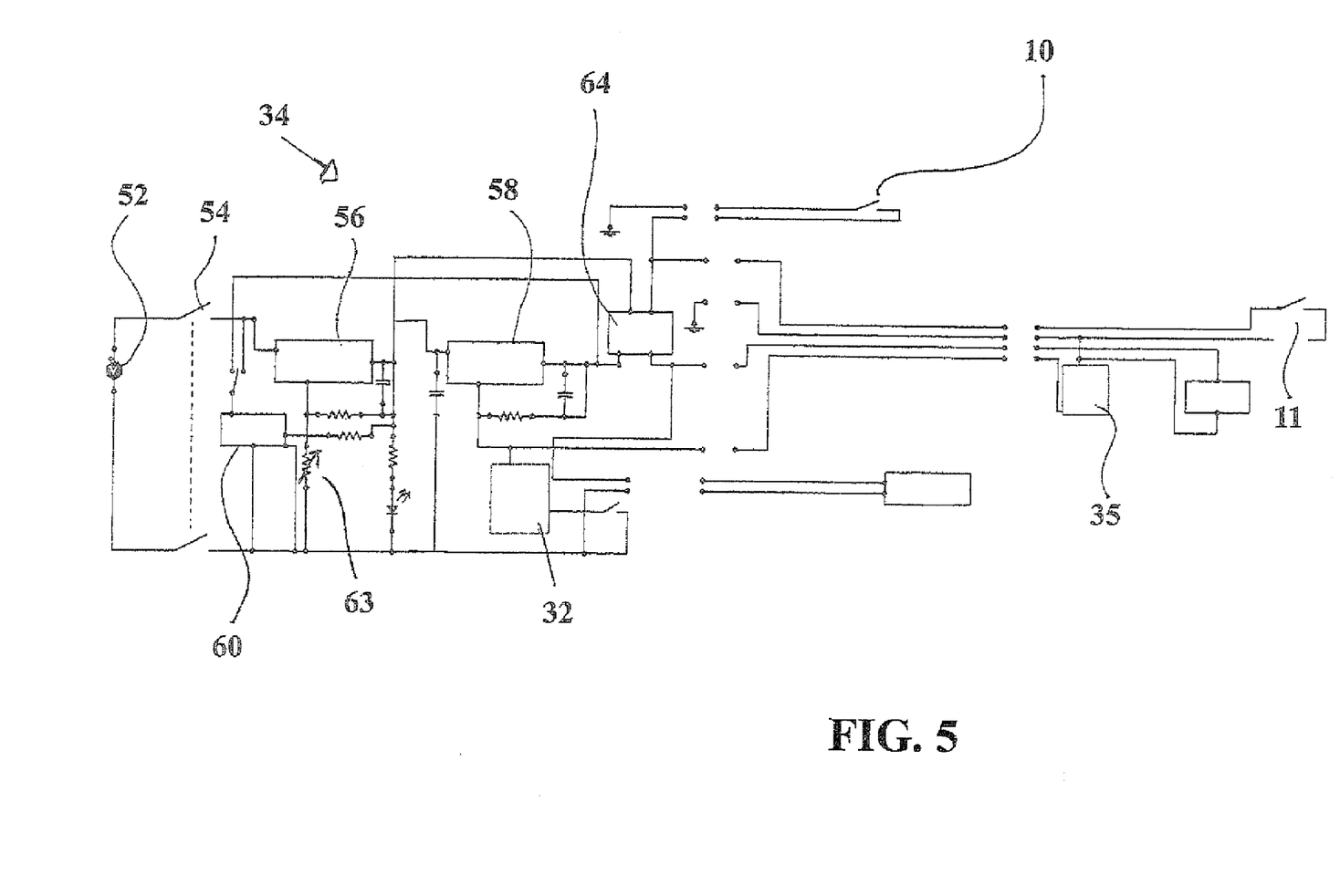
FIG. 5 is the electrical schematic for the retrofit control and DC power supply system.

The operational circuit 34 is best described looking at FIG. 5. Power comes in from the battery source 52 via the main power electronic switch 30 through ON/OFF relay 54 to the first voltage regulator 56 and then to the second voltage regulator 58. The circuit is completed (energized) to allow power to the spring clip power connector 40 (and tattoo gun 8) by either of the grounding out of current through the gun trigger switch 11 or the foot pedal 10. The first voltage regulator 54 adjusts the operating voltage of the control unit 6 for the operation of the voltmeter 60 and the solid state switches thereon. The second voltage regulator 56 maintains a stable voltage for the operation of the tattoo gun 8 (maintains constant voltage as the battery power is dissipated.) Power taken across voltmeter 60 provides a voltage readout of the battery condition or of the actual output power to the tattoo gun 8 by operation of battery status button 31. Power then proceeds through a transistorized voltage regulator 62 that adjusts the speed of the gun. This is a three prong regulator that has the middle prong connected to a potentiometer that adjustably bleeds the voltage to ground. (This is the potentiometer that is integrated into the spring clip power connector 40 or the speed adjustment buttons 32 built into the control unit 6.) Power then proceeds to the switching relay 64 that is energized to allow the circuit to complete through the tattoo gun motor after the ON/OFF power switch 30 or foot pedal 10 is activated.

The voltage is capped (limited) by the first voltage regulator 56. An internal voltage regulating potentiometer 63 adjusts the power going to the tattoo gun 8 such that it does not exceed the max voltage needed to run the tattoo gun 8.

Eventually it may be possible to mount the control unit/battery assembly to the gun itself as batteries miniaturize and the vibrate coils/relays of the gun become more efficient, requiring less voltage to operate. At this time to accomplish such a task would make a tattoo gun that is too bulky, heavy and unwieldy to work with.

The conventional method of vibrating the tattoo gun's needle utilizes a rapidly moving coil wrap motor. This coil can be replaced by stacked arrangement of piezoelectric motors 71 (piezo stacker electric motor) or a conventional motor and flywheel assembly that would still vibrate the needles in an up and down motion by the rapid vibration of a moveable bar connected mechanically to the needles.

Figure 6:
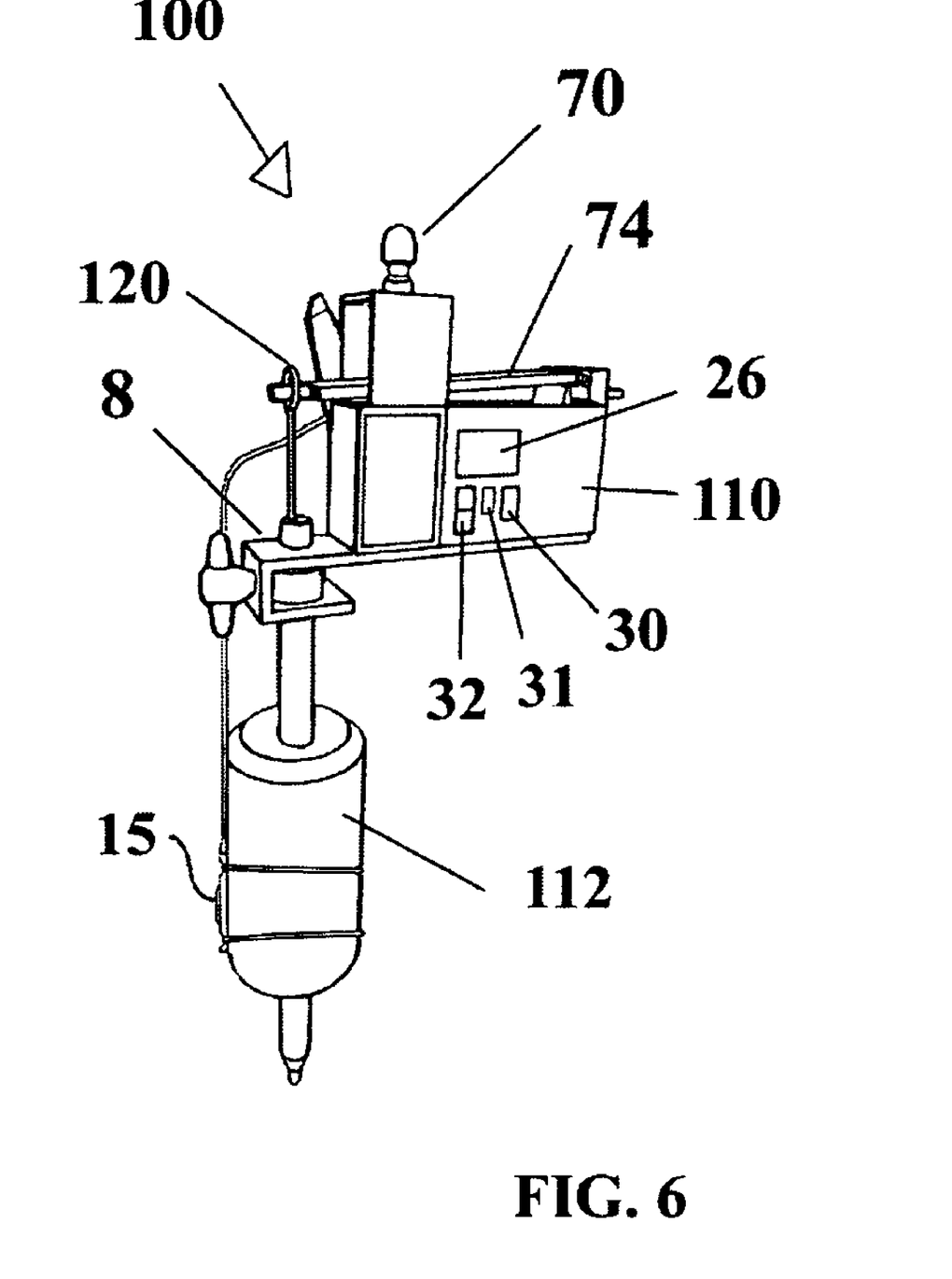
Figure 7:
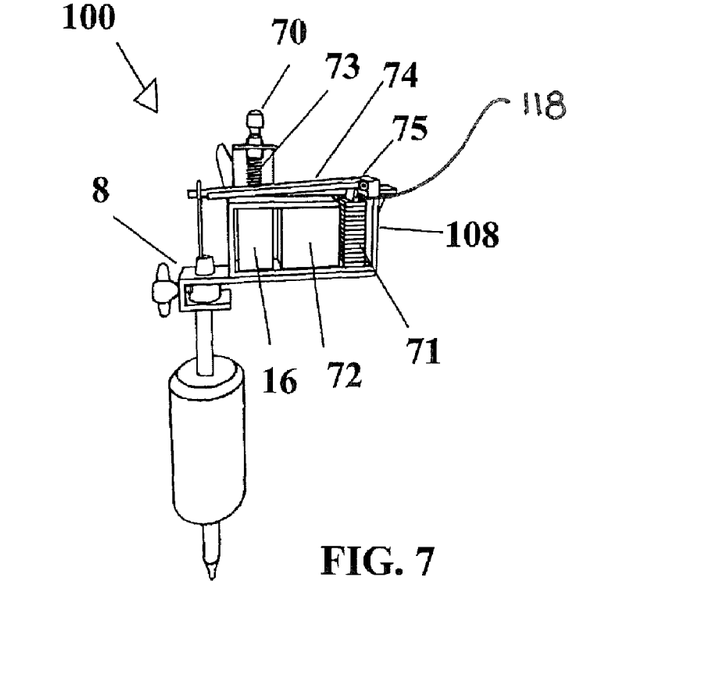
FIG. 7 illustrates the alternate embodiment retrofit control system and power supply for a tattoo gun with the side cover plate removed.
Figure 8:
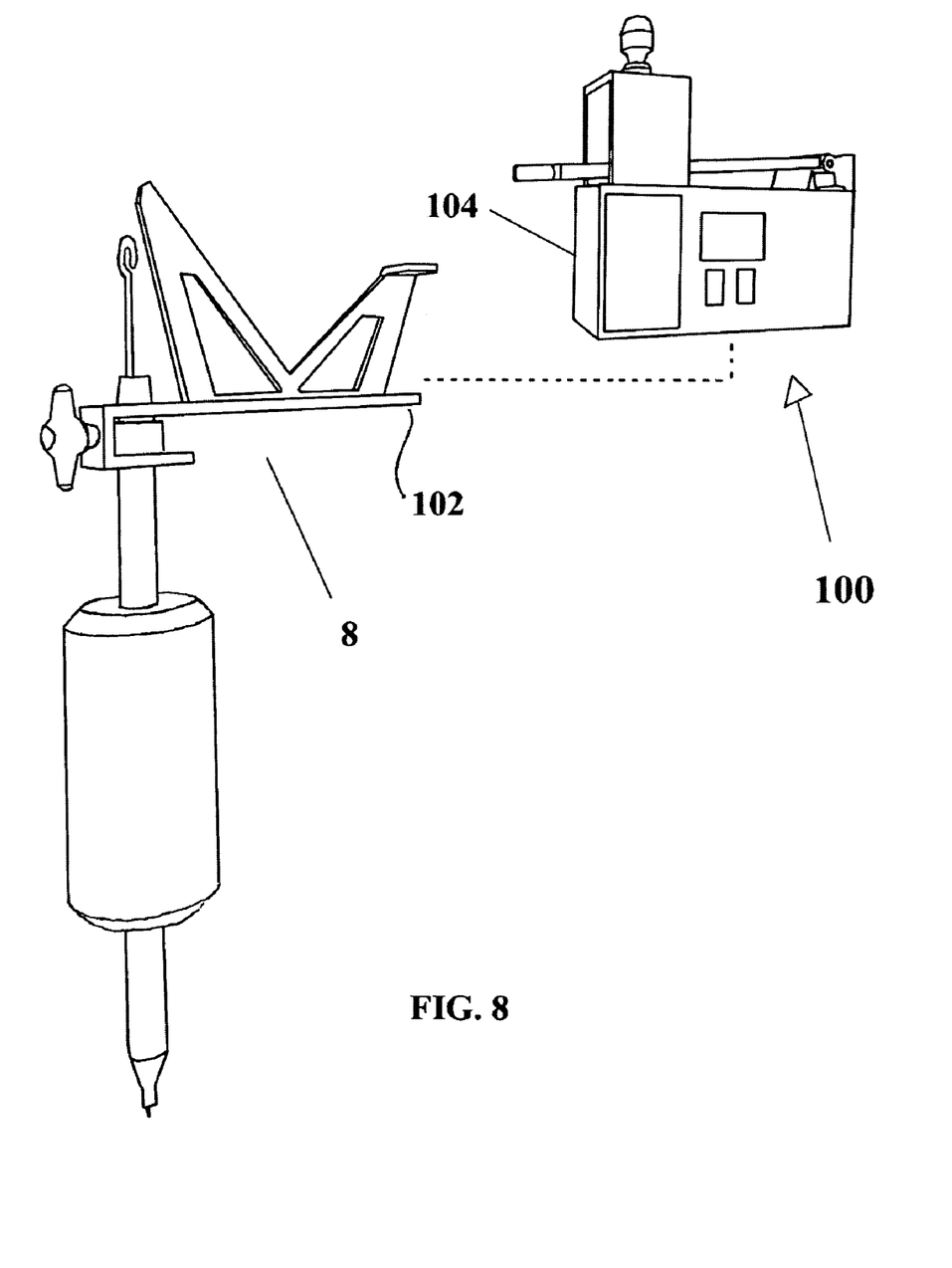
FIG. 8 illustrate the alternate embodiment retrofit control system and power supply for a tattoo gun prior to installation on a tattoo gun.

FIGS. 6, 7 and 8 illustrate the alternate embodiment retrofit control system 100 and power supply for a tattoo gun with the side cover plate on, with the side cover plate removed and prior to installation on a tattoo gun 8. In this embodiment the retrofit system 100 is self contained in case that is directly mounted onto the tattoo gun's 8 main support frame 102 by mechanical fasteners, preferably screws or nuts and bolts. The system case has a support base 73 from which a vertical support 108 extends normally. The system 100 is mounted on the gun 8 in place of the original magnetic coils. A voltage and frequency generator 72, the battery 16 and the piezo stacker electric motor are mounted in the system case 104 below the drive arm 74 which swings about the pivot 75 on the vertical support 108. The electronics (which function essentially similar to those of the preferred embodiment described herein and are also mounted onto a printed circuit board) reside on the case panel 110 on the side of the system case 104. The system electronics include main power electronic switch 30, display interface 26, battery status button 31 and needle speed control 32. Similar to the preferred embodiment, tactile switch 15 switches on and off the power to the gun 8 and is mountable anywhere on the gun 8 by mechanical means such as rubber bands, cable ties, glue or screws, however the likely location for mounting would be the top surface of the tattoo gun's barrel 112 where the artist's index finger could readily access it. A screw adjust means 70 affixed to the support base 73 adjusts the tension on spring 73 that controls the rebound of the drive arm 74 to adjust the force and speed of the needle.

The mechanical oscillation to drive the tattoo gun needle is generated by voltage coming from the battery 16 that enters the voltage/frequency regulator 72. There is a DC square wave generated at a frequency and voltage set by the user though needle speed control 32. This DC square wave of current travels to the piezo stacker motor 71 which expands vertically as the positive voltage is applied, and returns to its neutral (or compressed) thickness when the voltage returns to zero. When the piezo stacker motor 71 expands it pushes on the drive arm 74 with its fulcrum body 118 causing it to swing about pivot 75. The proximity of the fulcrum body 118 to the pivot 75 multiplies the movement of the piezo motor at the distal end of the drive arm 74. This oscillating movement is transmitted to the needle by virtue of the connection between the distal end of drive arm 74 and the distal arm of the needle 120.

It is to be noted that with this system the piezo stacker motor 71 only withdraws the needle and the screw adjuster means 70 and spring 73 control the insertion of the needle.

It is well known it the art that the location of the peizo electric motor 71 may be varied to different locations in the case (I.E. above the drive arm 74 to drive the arm down or on an section of the drive arm 74 extending beyond the pivot 75 to pivot it down.) Different spring locations and/or types may be used and batteries may be mounted in different locations depending on weight size and balance.

The above description will enable any person skilled in the art to make and use this invention. It also sets forth the best modes for carrying out this invention. There are numerous variations and modifications thereof that will also remain readily apparent to others skilled in the art, now that the general principles of the present invention have been disclosed. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Having thus described the invention, what is claimed as new and desired to be secured by Letters Patent is as follows:

1. A retrofit control unit and DC power supply for a tattoo gun comprising:
    a control unit housing a printed circuit board with a control logic circuit and components thereon, a visual display interface, a power switch, a battery status switch, voltage adjustment controls, a foot switch cable jack plug, a control cable pin connector receptacle, and a tattoo gun power cable jack plug:
    a removable battery mechanically engaged in said control unit;
    an electrical connector having a distal end with a first set of spring expandable conductor arms for engagement with said tattoo gun, a proximate end having a pin connector plug matingly conformed for connection with a pin connector affixed to a first end of a control cable, and a potentiometer voltage control for speed adjustment of said tattoo gun affixed thereon;
    said control cable connecting said control unit to said electrical connector, wherein said control cable has a pin connector affixed to a second end for connection with said control cable pin connector receptacle;
    a jack plug formed therein said electrical connector; and
    a detachable power switch for turning on or off said tattoo gun, affixed at a first end of an extension cable that has an electrical jack formed thereon a second end that is matingly conformed for engagement with said electrical connector's jack plug.

2. The retrofit control unit and DC power supply for a tattoo gun of claim 1 further comprising a belt clip affixed to a face of said control unit.

3. The retrofit control unit and DC power supply for a tattoo gun of claim 2 further comprising an elastic arm band with a pouch formed thereon adapted for housing said control unit.

4. The retrofit control unit and DC power supply for a tattoo gun of claim 1 further comprising:
    a foot switch attached at one end of a cord with the foot switch cable jack plug affixed at a second end of said cord adapted for mating insertion into said control unit's a foot switch cable jack plug.

5. A retrofit control unit and DC power supply for a tattoo gun comprising:
    a control unit housing a printed circuit board with a control logic circuit and components thereon, a visual display interface, a power switch, a battery status switch, a first power cable pin connector receptacle;

a removable battery mechanically engaged in said control unit;

a power cable having a first pin connector at a proximate end and a second pin connector at a distal end, and adapted for connecting said control unit to an electrical connector; and said electrical connector with a body having a distal end with a set of spring expandable conductor arms extending axially therefrom for engagement with matingly conformed contractors on a tattoo gun, a proximate end having a pin connector plug matingly conformed for connection with said first pin connector on said power cable, a potentiometer voltage control for speed adjustment of said tattoo gun affixed thereon a face of said body, and a tactile tattoo gun power switch affixed on said tattoo gun and connected at a first end of a switch extension cable having a second end removably connected to said body by a jack plug matingly conformed to a jack plug receptacle formed therein said body.

6. The retrofit control unit and DC power supply for a tattoo gun of claim 5 further comprising a set of voltage adjustment controls.

7. The retrofit control unit and DC power supply for a tattoo gun of claim 6 further comprising a foot switch cable jack plug.

8. The retrofit control unit and DC power supply for a tattoo gun of claim 7 further comprising a second power cable jack plug.

9. The retrofit control unit and DC power supply for a tattoo gun of claim 8 further comprising a belt clip affixed to a face of said control unit.

10. The retrofit control unit and DC power supply for a tattoo gun of claim 9 further comprising an elastic arm band with a pouch formed thereon adapted for housing said control unit.

* * * * *